United States Patent [19]

Hausman Hazlitt et al.

[11] Patent Number: 4,731,154

[45] Date of Patent: Mar. 15, 1988

[54] METHOD AND APPARATUS FOR QUANTITATIVE MEASUREMENT OF ORGANIC CONTAMINANTS REMAINING ON CLEANED SURFACES

[75] Inventors: Andrea Jo Hausman Hazlitt; Warren F. Richey, both of Lake Jackson, Tex.

[73] Assignee: The Dow Chemical Company, Midland, Mich.

[21] Appl. No.: 60,139

[22] Filed: Jun. 9, 1987

Related U.S. Application Data

[63] Continuation-in-part of Ser. No. 877,636, Jun. 23, 1986, which is a continuation-in-part of Ser. No. 821,933, Jan. 24, 1986, abandoned.

[51] Int. Cl.⁴ .................... B44C 1/22; B29C 37/00
[52] U.S. Cl. .................... 156/626; 134/113; 156/345; 156/668; 356/436
[58] Field of Search ............ 156/626, 627, 642, 345, 156/668; 134/57 R, 109, 113; 210/85, 96 R; 436/85; 356/36, 237, 436

[56] References Cited

U.S. PATENT DOCUMENTS

| 3,973,572 | 8/1976 | Brous | 134/57 R |
| 4,023,931 | 5/1977 | Wolfgram | 324/71 R |
| 4,530,601 | 7/1985 | Tasset | 356/36 |

OTHER PUBLICATIONS

W. F. Richey, et al., "New Analyses for Residual Rosin on Cleaned Electronic Circuit Boards", *Proc. Nepcon West '85*, Feb. (1985), 301–03.

L. J. Turbini et al., "A Comparison of Removal of Activated Rosin Flux by Selected Solvents", *IPC*, Sep. (1979).

E. Westerlopen, "Rosin Solder Flux Residues Shape Solvent Cleaning Requirements", *Electronic Packaging & Production*, Feb. (1985), pp. 118–174.

C. F. Coombs, Jr., *Printed Circuits Handbook*, 2nd Ed., McGraw-Hill Book Co., 1979, pp. 16-17 to 16-18.

H. H. Manko, "New Packaging Techniques Force a Reexamination of Cleaning Methods", Electronic Packaging & Production, Aug. (1984), 68–73.

S. L. Spitz, "Cleaning Printed Circuit Boards for Higher Quality: Electronic Packaging and Production, Sep. (1985), 100–106.

N. MacLeod, "The Rapid Testing of Ionic Contamination on Printed Wiring Boards and Assemblies", *Proc. Nepcon West*, vol. 1, Feb. (1986), 198–206.

J. K. Bonner, "A New Solvent for Post-Solder Cleaning of Printed Wiring Assemblies", *Proc. Nepcon West*, vol. 2, Feb. (1986), 763–774.

R. Aspandiar, et al., "Is OA OK?", Circuits Manufacturing, Apr. (1986), 29–36.

Operating Manual for the Alpha Ionograph ® System.

H. Cole, "Measurement of Surface Ionic Contamination", Society of Manufacturing Engineers, (1975), AD 75-366, 1–12.

Alpha Metals, Inc., 1983, Brochure.

Federated–Fry Metals, Inc., Bulletin 201, Feb. (1985).

W. G. Kenyon, "How to Use the Solvent Extract Method to Measure Ionic Contamination of Printed Wiring Assemblies", Insulation Circuits, Mar. (1981), 47–49.

(List continued on next page.)

*Primary Examiner*—William A. Powell
*Attorney, Agent, or Firm*—Joe R. Prieto

[57] ABSTRACT

An apparatus and method are disclosed for determining the cleanliness of an electronic circuit assembly (ECA) such as printed circuit boards (PCB) following normal cleaning and flux removal processes. The apparatus and method are used to quantitatively measure the organic contaminants such as the amount of rosin flux remaining on an ECA. The apparatus utilizes small volumes of isopropanol and a spectrophotometric analytical instrument. The apparatus generally provideds for washing the "cleaned" or defluxed ECA with a measured volume of isopropanol and thereafter measuring the organic contaminants in the wash solution by spectrometric analysis. The results can then be compared to a standard.

39 Claims, 6 Drawing Figures

OTHER PUBLICATIONS

Kenco Alloy & Chemical Co., Inc., Omega Meter ® II System, Bulletin 379.

Kenco Alloy & Chemical Co., Inc., Omega Metal ® II Model 300, Operators Manual, 1979.

R. J. DeNoon, et al., "Detection of Ionic Contaminants on Printed-Wiring Assemblies", Naval Avionics Facility, MRR No. 3-72.

Institute of Printed Circuits, Test Methods Manual, No. 2.3.38 1/83, 1-5, and No. 2.3.39 1-7.

D. Sanger et al., "A Study of Solvent and Aqueous Cleaning of Fluxes", Naval Weapons Center, NWC TP 6427, Feb., 1983, pp. 1-108.

Guided Wave, Inc., The Optical Waveguide Spectrum Analyzer.

METHOD AND APPARATUS FOR QUANTITATIVE MEASUREMENT OF ORGANIC CONTAMINANTS REMAINING ON CLEANED SURFACES

CROSS REFERENCE TO THE RELATED APPLICATION

This is a continuation-in-part of application Serial No. 877,636, filed June 23, 1986, now pending, which is a continuation-in-part of application Ser. No. 821,933 filed Jan. 24, 1986, now abandoned, both applications are incorporated herein by reference.

BACKGROUND OF THE INVENTION

This invention relates to a method and apparatus for measuring the organic contamination of an electronic circuit assembly, for example a printed circuit board.

The cleanliness of electronic circuit assemblies (ECA), such as printed circuit boards (PCB), is generally regarded as being critical to their functional reliability. Ionic and nonionic contamination on circuit boards are believed to contribute to premature failures of the circuit boards by allowing short circuits to develop.

In the manufacture of electronic circuit assemblies, ionic and nonionic contamination can accumulate after one or more steps of the process. Circuit board materials are plated, etched, handled by operators in assembly, coated with corrosive or potentially corrosive fluxes and finally soldered. Of course, there is cleaning at various steps along the way—for example after plating, etching and soldering—but each step, nevertheless, represents a potential source of ionic and nonionic contamination which may be carried over on surfaces of the finished circuit. It is therefore most important that a thorough cleaning of the surfaces be achieved after soldering. This is probably the last opportunity to remove ionic and nonionic contamination accumulating on the circuit in the manufacturing processes.

It is common to evaluate the level of ionic contamination on an assembled board by a solvent extraction test. The board to be tested is washed with an isopropanol/water mixture which is then subjected to an electrical conductivity/resistivity measurement from which an ionic concentration is calculated and expressed as a quantity of sodium chloride per unit area of board surface.

Until now there has been no simple quantitative analysis for the organic contaminants on a cleaned ECA. "Organic contaminants" herein includes ionic and nonionic contaminants which are not detectable by conductivity/resistivity measurements known for measuring ionic contamination. In order to better study the effectiveness of various solvents in removing the organic contaminants such as rosin flux from soldered boards, it is desired to provide a method and apparatus for determining the residual organic contaminants such as rosin flux on an ECA. It is further desired to provide a method and apparatus for substantially automatically and continuously determining the quantity of organic contaminants on an ECA. It is further desired to provide a method and apparatus for determining organic contaminants down to concentrations of about 1 microgram per square inch.

BRIEF DESCRIPTION OF THE INVENTION

One aspect of the present invention is a method for determining the cleanliness of electronic circuit assemblies (ECA) including:

(a) contacting a previously defluxed ECA with a solvent suitable for removing organic contaminants on the surface of the ECA, (b) measuring the spectral absorption of the organic species in the solvent contacted with the ECA in the UV or visible region, and (c) comparing the resultant absorbance value to a standard.

Another aspect of the present invention is an apparatus for substantially automatically, continuously and quantitatively measuring organic contamination such as residual rosin on electric circuit assemblies (ECA) comprising:

(a) a means for substantially continuously contacting a previously defluxed ECA with a solvent, and (b) a means for substantially continuously measuring the spectral absorbance of the organic contaminant species in a continuous stream of the solvent contacted with the ECA.

Another embodiment of the present invention is an apparatus for quantitative analysis of organic contamination on ECA including:

(a) a vessel adapted for receiving an ECA and a measured quantity of solvent for washing the ECA;

(b) a means for recirculating the solvent to the vessel;

(c) a monitor means adapted for measuring the spectral absorption levels of the organic contaminants in the recirculated solvent; and (d) a means for recording the absorbance units measured by the monitor means.

BRIEF DESCRIPTION OF THE DRAWINGS

This invention will be better understood by reference to the FIGS. 1-6 herein, wherein the preferred embodiments of the present invention are illustrated and wherein like reference numerals refer to like parts in the different figures.

DETAILED DESCRIPTION OF PREFERRED EMBODIMENTS

Figure 1:
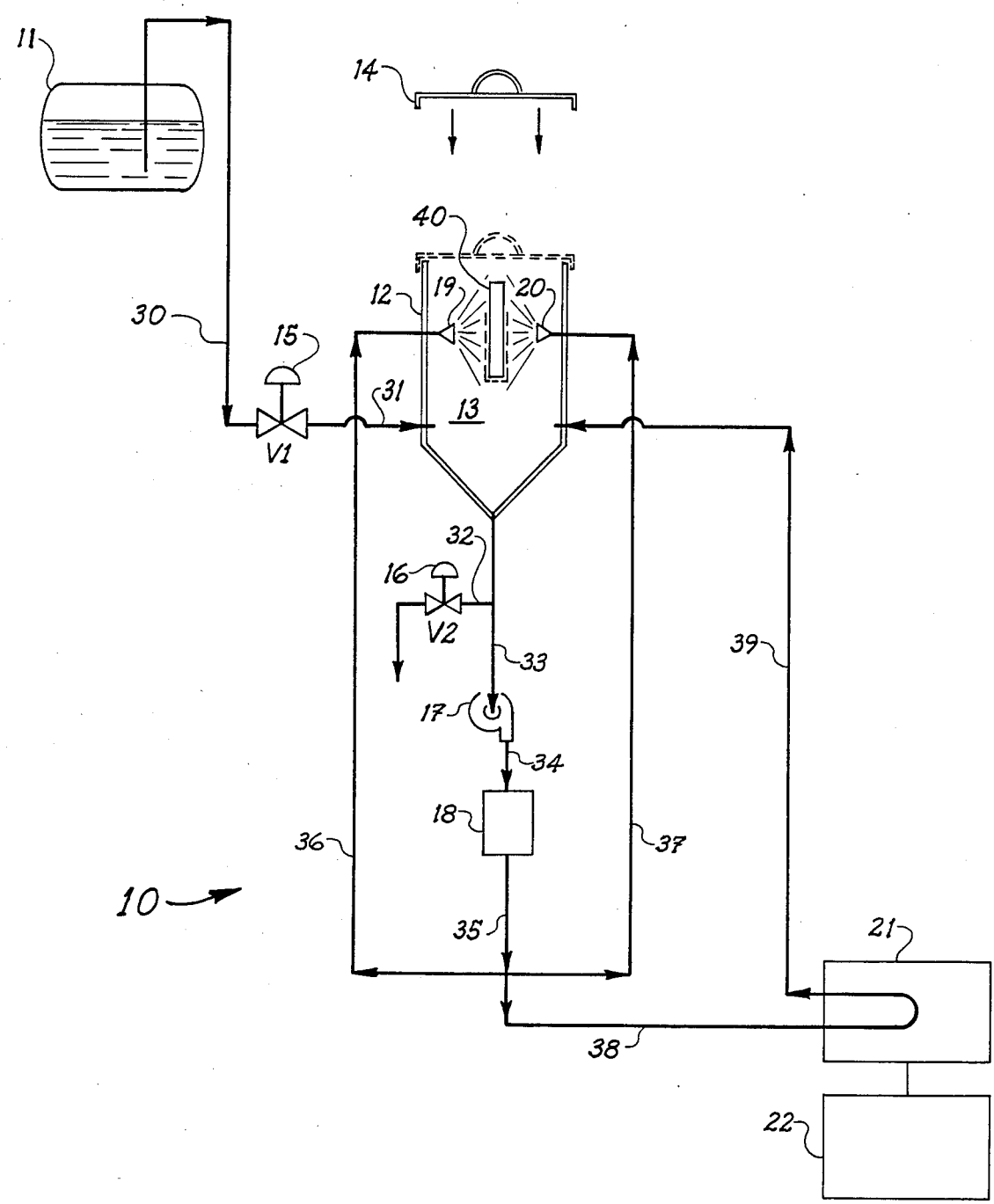
FIG. 1 is a schematic illustration of the apparatus of the present invention.

The method and apparatus of the present invention is useful in determining the organic contamination on the surface of electronic circuit assemblies (ECA), for example, printed circuit boards. Such boards are customarily cleaned after soldering operations, which cleaning operation is to remove as much as possible of the various contaminants which are caused by the soldering process. Organic contamination can cause subsequent corrosion if not removed from the printed circuit board.

The cleaning processes used by the manufacturers of printed ciruit boards normally will provide substantially clean boards. The present invention is directed to a means for testing the reliability of such cleaning processes.

In the present invention, absorption spectroscopy, particularly in the ultraviolet (UV) and visible regions, is the basis for the quantitative analysis of the organic contaminants present on the surface of ECA's. Any organic contaminant which is (1) soluble in a solvent which, in turn, is transparent in the portion of the ultraviolet or visible region of interest and (2) which absorbs energy in the ultraviolet or visible region of the spectrum may be quantified in accordance with the method and apparatus of the present invention. The maximum wavelength of the absorbing organic contaminant species is measured in the region of interest which may lie in the range of about 190 nanometers (nm) to about 800 nm.

Residual organic contaminants which are likely to be found on ECA and which can be measured by the method and apparatus of the present invention include, but are not limited to, for example, rosin flux, photoresist, solder masks, adhesives, machine oils, greases, silicones, lanolin, mold release, polyglycols and plasticizers. Generally, the organic contaminants of the present invention are nonionic. Some contaminants for example, abietic acid, measured by the present method may dissociate slightly in some solvents and therefore may be considered partially ionic. However, for purposes of measurement by the method of the present invention, the term "organic contaminants" includes such slightly ionic contaminants and other ionic contaminants which can not be measured or detected by conductivity/resistivity measurement known by those skilled in the art for measuring ionic contamination.

Examples of organic contaminants and their characteristic wavelengths are described below in Table I.

TABLE I

| Contaminant | Solvent | Wavelength (nm) |
| --- | --- | --- |
| 1. photoresist Resiston ® made by DuPont De Nemours, E.I., Inc. | methylene chloride | 622 |
| 2. solder mask Wondermask ® made by Techspray of Amarillo, Texas | isopropanol | 220 plus weak band at 275 |
| Vacrel ® 930 made by DuPont De Nemours, E.I., Inc. | isopropanol | 226, 252, shoulders 278 and 282, broad weak bank centered on 350 |
| 3. adhesives rubber-based such as found on FasTape C ® made by Fasson Industrial Division of Avery International | isopropanol | 220 plus peak spikes at 265, 275, weak band at 410, shoulders at 240, 250 |
| silicone such as found on Kapton ® tape sold by 3M Co. | isopropanol | 220, broad shoulder at 262 |
| 4. silicones adhesives (see above) rubber such as Silastic ® 732 RTV | isopropanol (partially soluble) | broad band 235 to 220 |

TABLE I-continued

| Contaminant | Solvent | Wavelength (nm) |
| --- | --- | --- |
| Dow-Corning Corp. oil such as Fluid 200 made by Dow-Corning Corp. | isopropanol | marked increase in baseline even at 400, increased slope between 300 and 200 |
| 5. plasticizers such as found in polyethylene films/bags | isopropanol | increased slope in baseline at about 240 |

The present invention will be described herein with regard to the measurement of rosin flux. It is to be understood, however, that any organic contaminant, as described above, can be measured according to the present invention. Rosin fluxes consist primarily of natural gum rosin in an organic solvent. A major component of these fluxes is gum rosin, a major component of which is abietic acid which shows an ultraviolet absorbance maximum at about 242 nm, it being understood that published data sets the absorbance at 241.7 nm. This absorbance is the basis for the spectrophotometric method of determining the quantity of residual rosin on a cleaned, printed wiring assembly.

In one embodiment of the present invention for carrying out the determination of the amount of organic contaminants, for example rosin flux, remaining on a cleaned ECA, a defluxed board to be tested is placed in a suitable container such as an antistatic sealable flexible or rigid plastic container of appropriate size. Then, an accurately measured amount of a suitable solvent for washing the ECA is added to the container. Care should be taken in selecting the plastic container as plasticizers can be leached from the plastic by the solvent. Glass or metal containers could also be used in some cases. The container with the board and solvent is sealed and shaken for 10 minutes either manually or mechanically.

Then the absorbance of an aliquot of the wash solution in the desired ultraviolet or visible region is measured and compared to that on a standard curve of absorbance versus concentration. The standard curve is obtained by measuring a series of standard solutions containing known amounts of contaminants thereby to provide a calibration curve conforming to Beer's Law.

$$A = a\,b\,c$$

wherein,
A = Absorbance
a = specific absorbance (molar absorptivity)
b = path length of light
c = concentration of absorbing species.

The points on the calibration curve, when plotted, should fall on a straight line which passes through zero. Beer's Law is a limiting law and should be expected to apply only at low concentrations. At higher concentrations the refractive index of the chemical species being measured may vary or the chemical species may form molecular associations causing nonlinearity in the relationship between absorbance and concentration. The nonlinear curve is still useful in quantitative analysis, but the concentration of the analyte must be read from a standard curve which is verified at frequent intervals. The concentration obtained from the standard curve is converted into a contamination level in micrograms per square inch by use of the following equation:

$$\text{Residual organic contaminant} \left(\frac{\text{micrograms}}{\text{inch}^2}\right) = \frac{\left[\text{organic contaminant concentration}\left(\frac{\text{micrograms}}{\text{gm solvent}}\right)\right] \times \left[\begin{array}{c}\text{solvent sp. gr. or}\\ \text{density (gm/ml)}\end{array}\right] \times \left[\begin{array}{c}\text{vol solvent}\\ \text{(ml)}\end{array}\right]}{\text{total surface area of board (inch}^2)} \quad \text{Equation I}$$

Another equation useful for converting concentration obtained form the standard curve to a contamination level in micrograms per square inch is as follows:

$$\text{Residual organic contaminant}\left(\frac{\text{micrograms}}{\text{inch}^2}\right) = \frac{\left[\text{organic contaminant concentration}\left(\frac{\text{micrograms}}{\text{ml solvent}}\right)\right] \times \left[\begin{array}{c}\text{vol solvent}\\ \text{(ml)}\end{array}\right]}{\text{total surface area of board (inch}^2)} \quad \text{Equation II}$$

The solvents used in the present invention should be capable of dissolving the contaminant species of interest and have transparancy such that the absorption of the solvent is at least about 20 nm less than the maximum adsorption of the organic species of interest. Preferably, the solvent is nontoxic and nonflammable. In addition, the solvent should have a boiling point less than about 100° C. to facilitate its removal from circuit board surfaces by evaporation or by heating slightly. The solvent used, preferably, may be a high purity polar solvent, such as isopropanol, or an aqueous solution of the solvent containing up to about 25% deionized water.

For example, for residual rosin measurements, solvents which are deemed suitable, i.e. having the requisite UV-visible transparency and solvency for the solids, includes the well known and widely used isopropanol, either High Performance Liquid Chromatographic grade (HPLC) or Spectral Grade (SG), ethanol and trifluoroethanol. Other polar solvents such as acetonitrile, isobutyl alcohol, methanol, propronitrile which are capable of dissolving at least abietic acid, and preferably all the organic solids of a flux formulation, and having a boiling point preferably below about 100° C. can be used. Higher boiling point solvents such as butyl alcohol, butyronitrile and, isopentyl alcohol could be used if application of heat is not detrimental. While solvents such as p-dioxane or ethyl ether may be used, the former may have toxicity problems and both the former and latter could create a fire hazard.

Accurate and reliable results can be obtained using the above general procedure, more specifically described in Example 1 below, but time-consuming manual steps are required in the overall process. A more preferred embodiment of the present invention is a substantially automated system for measuring the organic contaminants on an ECA, the method which is described more specifically below and in Examples 2-20.

FIG. 1 shows an apparatus, generally indicated by numeral 10, for substantially automatically, continuously and quantitativly measuring the organic contamination such as rosin flux on electronic circuit assemblies (ECA) 40 which have been cleaned or defluxed after the soldering steps in their manufacture. A solution reservoir 11 containing a solvent suitable for washing the ECA 40 is connected to a vessel 12 with a chamber 13 adapted for receiving a test sample of the ECA to be evaluated. The vessel 12, is also adapted for receiving a measured quantity of the solvent for washing the ECA.

The shape of the vessel 12 may be any shape desirable adapted for holding an ECA such as a printed circuit board. It is preferred, however, that the shape of the vessel be such that the quantity of solvent required for washing of the ECA is minimized. In this instance, the vessel 12 is a cylindrical-shaped housing or tank with a cone-shaped bottom and an open top which preferably contains a removable liquid-tight cover 14.

A measured quantity of liquid from the reservoir 11 is conducted to the vessel 12 via a conduit 30 and 31 through valve 15. When the measured amount of solution from the reservoir 11 is transfered into the vessel 12, the valve 15 is used to stop flow of solution from the reservoir 11 to the vessel 12. A drain line 32 and valve 16 may be used to remove solution from the chamber 13.

The liquid is passed to pump 17 throuqh line 33. The pump 17 is used for recirculating the solution in vessel 12 through the chamber 13. The solution in vessel 12 passes through pump 17 via line 34 and, preferably, circulates through a filter 18 to remove any particles or solid material present in the solution. In FIG. 1, there is shown the liquid passing through the filter 18 and circulating to the vessel 12 via conduits 35, 36, and 37 to two spray nozzles 19 and 20. It is to be understood, however, that any number of spray nozzles with corresponding conduits from the pump 17 may be incorporated into the vessel 12 and the "recirculation loop" consisting of conduits 33–37, inclusive. The spray nozzles are used to spray solution onto the surface of the ECA to solubilize surface contamination.

A sidestream 38 of the solution is conducted to a means for measuring the spectral absorbance of the side stream such as a monitor or spectrophotometer 21, preferably with a signal sensing means such as a recorder 22 for recording the output of the monitor.

The monitor 21 is adapted for measuring the absorbance in the ultraviolet (UV) or visible region of the spectrum of the organic contamination such as rosin flux contained in the side stream solution. Preferably used are UV-visible monitors containing a flow-through quartz cell. Any conventional UV-visible monitor capable of measuring the requisite absorbance may be used. For example, a spectrophotometer capable of measuring absorption at about 242 nm is required for analysis of rosin flux. For other organic contaminants it is preferable to use a spectrophotometer with the capability of measuring the absorbance for the specific contaminants. To provide greater flexibility in setting the desired wavelength, it is preferred to use a variable wavelength UV-visible monitor, which is capable for example of measuring wavelengths in the range of about 190 nm to about 800 nm.

The liquid sidestream 38 is passed through the monitor 21 and is continuously pumped to the vessel 12 via conduit 39. The solution being circulated through the vessel continuously removes remaining contamination from the ECA which is sensed by the UV-visible monitor and is evaluated by a signal sensing means 22 connected to the monitor 21. The liquid circulates through the vessel 12 to remove any remaining contamination on the ECA until the reading accomplished by the signal sensing means 22 reaches a stable maximum, indicating that the extraction of the contaminant is completed and equilibrium has been achieved.

Another spectroscopic monitoring device employing fiber optics, such as of the type manufactured by Guided Wave, Inc. of Eldorado Hills, Calif. and sold under the tradename Optical Waveguide Spectrum Analyzer, could be used to measure the absorbance in the instant procedure as an alternative to the UV-visible spectrometer and flowthrough quartz cell described herein. A fiber optics probe could be placed directly into the solution in the sample chamber 13, thus eliminating the need for taking a sidestream of the circulatinq solution through a flow-through cell for the absorbance measurement.

The apparatus in FIG. 1 measures residual organic contaminants on electronic circuit boards by monitoring the absorbance of a solvent extract, made by contacting the specimen board with the solvent, at a wavelength appropriate for the contaminant of interest. The solvent is recirculated by a pump in repeated contact with the specimen, usually by spraying, until a constant maximum absorbance is indicated by the monitor, a UV-visible detector and recorder. At this point, the analysis is complete and the spent solvent is drained from the apparatus. After a period of several measurements the quantity of spend solvent can increase substantially, creating a disposal problem, as well as wasting potentially reuseable solvent and hence, can become uneconomical. The instrument in FIG. 1, therefore, can be modified to include one or more absorbing beds for removing organic contaminants from the solvent after the solvent is used and thus, the useful life of the solvent is extended. In addition, by using the absorption beds in the apparatus, the solvent waste disposal problem is greatly minimized.

Figure 2:
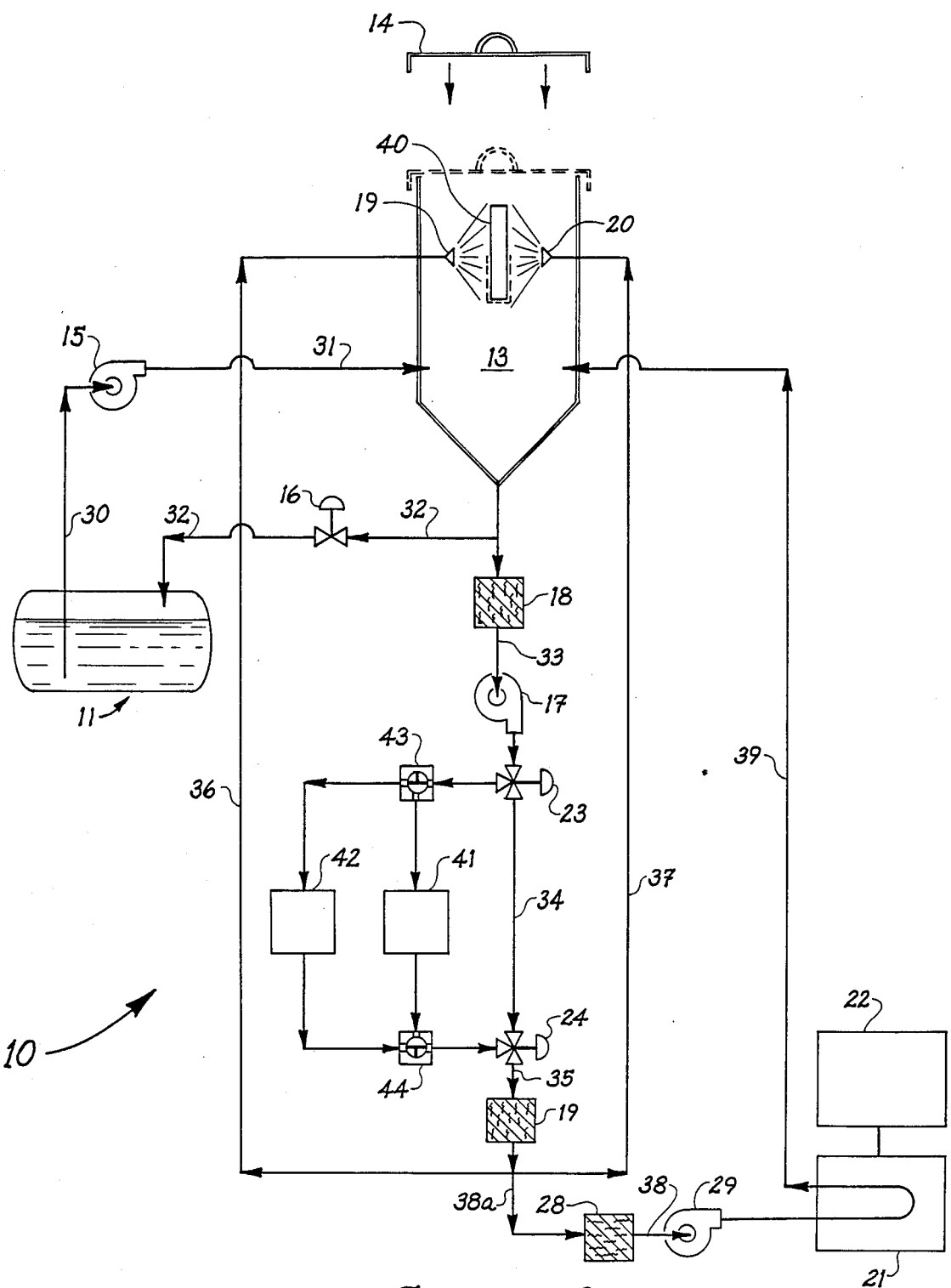
FIG. 2 is a schematic illustration of another embodiment of the apparatus of the present invention.

Another embodiment of the present invention incorporating the absorption columns for removing organic contaminants from a solvent is shown in FIG. 2, wherein an apparatus generally indicated by numeral 10, automatically and quantitativly measures the contamination, for example, on electronic circuit assemblies which have been cleaned or defluxed after the soldering steps in their manufacture. While other modifications to the apparatus in FIG. 1 can be made and are useful in carrying out the process of the present invention, the method shown in FIG. 2 is the most preferred embodiment.

The apparatus in FIG. 2, is substantially the same as the apparatus of FIG. 1, except that a set of absorption columns 41 and 42 are added to the fluid circulation loop. The absorption beds are used to remove organic contaminants from the circulating solvent to clean the solvent. In addition, in FIG. 2, the measured amount of solution from the reservoir 11 in the vessel 12, may be recycled back to the reservoir using a return line 32 and valve 16.

The apparatus of FIG. 2 further includes a separate pump such as a metering pump or high pressure liquid chromatography pump 29 which is used to pass the sidestream 38 and 38a to the monitor 21 through a filter 28.

The filter 18 is positioned before a pump 17 for removing any particles in the solution leaving the vessel 12. The pump 17 is used for recirculating the solution in the chamber 13. The solution leaving the pump 17 is filtered by the second filter 19 to remove any particles in the solution. The liquid passing through the filter 18 is circulated to the vessel 12 via conduits 33, 34, 35, 36 and 37 to spray nozzles 19 and 20.

The sidestream 38 and 38a of the solution is conducted to a UV monitor 21, preferably with a recorder 22 for recording the output of the monitor. The monitor 21 is adapted for measuring the absorbance of the contamination such as rosin contained in the wash solution. The liquid from the monitor 21 is continuously pumped using a third pump 29 to the vessel 12 via conduit 39. The filter 28 is positioned prior to pump 29 for removing particulate material in the solution. The solution circulated through the vessel continuously removes remaining contamination from the ECA which is sensed by the UV monitor and is evaluated by a signal sensing means connected to the monitor; the liquid circulates through the vessel to remove any remaining contamination until the reading accomplished by the signal sensing means indicates a particular predetermined level.

A valve 23 is used to divert flow through two columns, columns 41 and 42 respectively. Column 41 and 42 contain absorbent material for organics such as activated charcoal for removing organic from the solvent. Threeway valves 43 and 44 are used to alternatively use one column while one column is on standby. A valve 24 is used to return flow from columns 41 or 42 to stream line 35.

With reference to FIG. 1, again, carrying out an embodiment of the method of the present invention, a defluxed board to be tested is placed in the vessel 12 of appropriate size, and an accurately measured amount of solvent such as isopropanol is added to the vessel from the reservoir 11.

The quantity of solvent used depends on the level of contamination on the ECA and its surface area. For measuring contaminant levels of 50 ppm or less, a convenient quantity of solvent used may be from about 0.5 milliliter (ml) to about 10.0 ml per square inch (in) of board. A convenient quantity of solvent for a first trial is about 3 milliliters per square inch (ml/in) of board.

As aforementioned, the quantity of solvent used depends on the level of contamination on the ECA. For example, if the level of residual rosin is so high that a solution with greater than about 50 ppm rosin is obtained by the procedure of this invention, additional solvent should be measured and added to the sample chamber to achieve a solution with an absorbance reading within the linear portion of the calibration curve. The nonlinear portion of the curve may be used to quantitate the higher levels of contamination only when the curve is verified at frequent intervals. Hence, it is more convenient to dilute the solution as described herein so that the absorbance falls in the more stable, more easily calibrated linear region of the curve. Alternatively, it may be judged that an ECA with such a high level of contamination is unacceptable and a quantitative result is unnecessary. Similarly if the contamination level is so low that it is difficult to detect, the ECA may be judged sufficiently clean. However, if quantitative results are desired, the volume of solvent per surface area of ECA may be effectively decreased in some cases by placing more than one ECA in the sample chamber to be simultaneously or serially extracted by the solvent and/or by reducing the total volume of the solvent to the limit imposed by the circulating system.

Once the desired volume of fluid has been placed within the vessel 12, the pump 15 is shut off. Thereafter, the pump 17 is started and the solution is continuously circulated through the vessel. The solution is sprayed onto the ECA via spray nozzles 19 and 20 provided in the chamber 13 of the vessel 12. In another embodiment, the ECA may be immersed in the vessel and an agitation means such as ultrasonic waves may be used, to remove any remaining contamination on the ECA. Substantially simultaneously a continuous sidestream is conducted from the recirculation loop to a quartz tube of a UV-visible monitor. The UV or visible absorption level of the contaminants in the wash solution is measured as the sidestream passes through the quartz tube cell of the UV-visible monitor and the sidestream is circulated back to the vessel 12. The recording means 22 is used to record the absorbance units from the UV-visible monitor.

The temperature of the circulating solution is generally maintained at about 30° C. Increases in temperature tend to shift absorption bands to longer wavelengths. To allow correction for possible wavelength drift and resultant inaccuracies in absorbance readings, the temperature of the circulating solution should be monitored and, preferably, controlled at about 30° C.±5° C.

All of the portions of the apparatus in contact with the solvent is preferably made of material which will not corrode or react with the solvent used in the process. For example, stainless steel is used for the reservoir, vessel and the conduits.

The absorbance of the wash solution is measured at the requisite wavelength and compared to that on a standard curve of absorbance versus concentration for the organic contaminant. The concentration obtained from the standard curve is converted into a contamination level in micrograms per square inch by use of Equation I or Equation II as described previously.

Generally, organic contaminants can be reliably measured by UV-visible spectroscopy to about 1 ppm or below. For example, in the case where the volume of wash solvent is about 1 ml per square inch of board and rosin flux is being determined, the level of contamination which can be measured is about 0.8 microgram per square inch. Improvements in spectroscopic technology could, of course, improve the sensitivity of measurements as could reducing the volume of solvent relative to board surface area.

With regard to FIG. 1, again, at the completion of a measurement cycle, the used solvent can be discarded through the stream line 32 and valve 16. For recovering the solvent and reusing the solvent of after a completed measuring cycle, the system in FIG. 2 is preferably used as described above.

Figure 3:
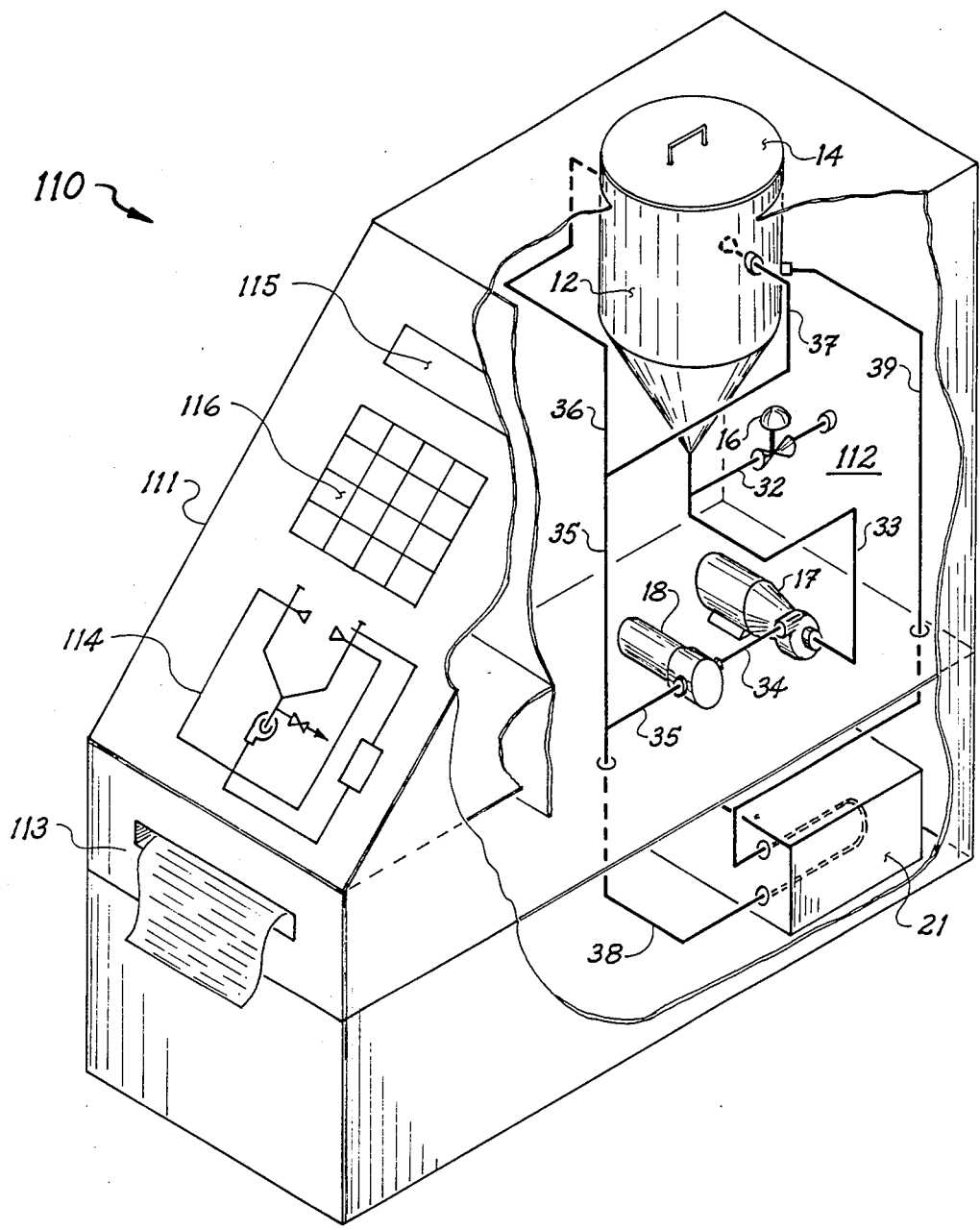
FIG. 3 is a perspective view, partially in section and partially cut away, of another embodiment of the apparatus of the present invention.

FIG. 3 shows an instrument, generally indicated by numeral 110, for detecting the organic contamination on an ECA. In this embodiment a housing 111 is used to enclose various portions of the apparatus described above and shown schematically in FIG. 1. The same numerical designation used in FIG. 1 is used in FIG. 3 to refer to identical elements. A portion of vessel 12, pump 17, filter 18 and the recirculation loop consisting of lines 32-37, can be enclosed in a flame-proof and air-tight compartment 112. The monitor 21 with a flow-through cell is connected to a printer or microprocesser 113 for recording the absorbance of a circulated solution. The housing 111 can contain any number of displays 114 and 115 for displaying data to an operator of the instrument. A keyboard means 116 for entering data for the operation of the equipment can also be incorporated into the instrument. The printer 113 may be used to print information and data generated by the instrument. The various displays, printers and keyboard means are known in art. However, the combination of these elements with the apparatus shown in FIG. 1 is novel. The instrument in FIG. 3 can be modified to include any number of absorption columns (not shown) for recovering spent solvent and recycling the recovered solvent as described above.

Figure 4:
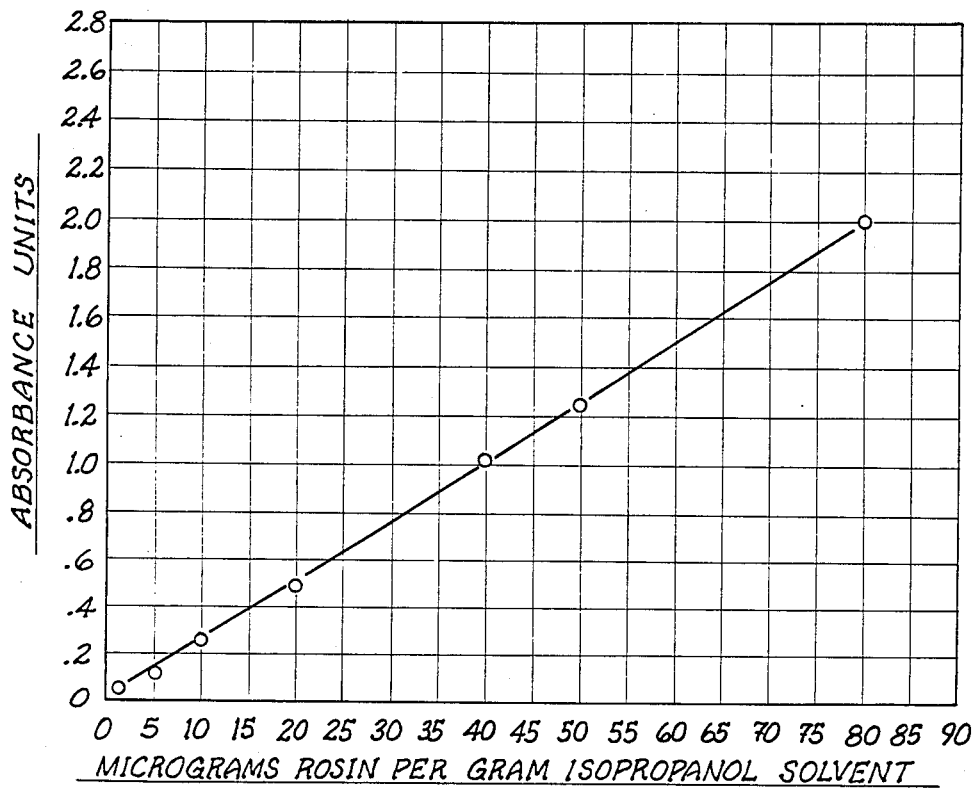
FIG. 4 represents a typical calibration curve showing micrograms of rosin per gram of solvent versus absorbance units.
Figure 5:
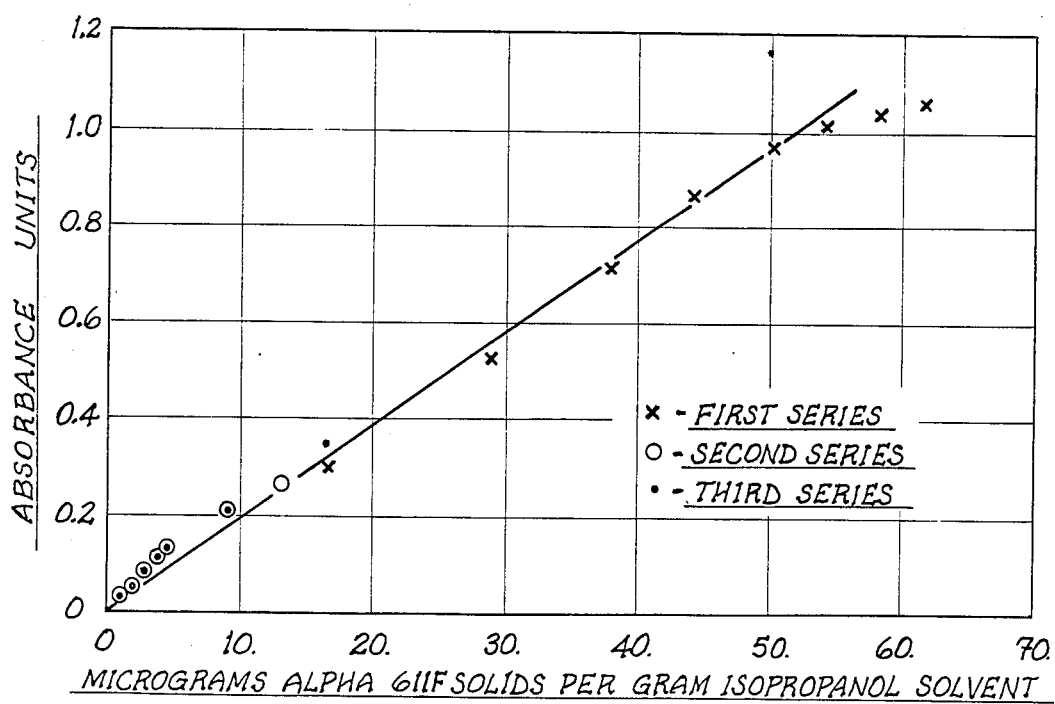
FIG. 5 represents a typical calibration curve showing micrograms of the residual nonvolatile portion of a commercial solder flux per gram of solvent versus absorbance units.

The following examples are illustrative of the present invention. While parts per million (ppm) is strictly defined as micrograms solute per grams of solution, in the examples, "ppm" for the standard solutions means micrograms solute per grams solvent (as shown in FIGS. 4 and 5). Since the contribution of the solute weight to the total weight of the solution was so small, it was judged to be negligible.

EXAMPLES 1-16

The following general procedures were followed to carry out the determination of the amount of rosin flux residue remaining on a "cleaned" ECA. By "cleaned" ECA it is meant that the ECA has been defluxed or has been subjected to a process for removing solder flux.

Preparation of Standard Solutions

About 0.0785 grams of gum rosin, or rosin flux solids obtained by removing the volatile solvent from a commercial rosin solder flux, was weighed exactly and then quantitatively transferred to 1-liter volumetric flask using High Performance Liquid Chromatographic (HPLC) or Spectral Grade isopropanol (sold by J. T. Baker Chemical Company labelled Baker "Analyzed"). Sufficient isopropanol was added to the flask to fill it to within 1 inch of the calibration line on its neck. The rosin was dissolved and the solution thoroughly mixed by vigorously shaking and inverting the stoppered flask several times. The stoppered flask with solution was allowed to sit for about 30 minutes to allow liquid to drain from the neck of the flask. Additional isopropanol was added dropwise to bring the volume just to the 1-liter mark and the stoppered flask was again vigorously shaken and inverted to thoroughly mix the contents. The density of the solution was taken to be approximately equivalent to the density of the solvent, which is 0.785 grams/milliliter at 20° C., because the contribution of the solute to the density of the solution was considered so small as to be negligible. Hence the concentration of the stock solution containing 0.0785 grams of rosin is 100 parts per million (ppm) or 78.5 micrograms per milliliter. Dilutions, called standard solutions, were prepared from this stock solution for use in obtaining the calibration curve of micrograms of gum rosin per gram isopropanol solvent versus absorbance units given in FIG. 4. Using an appropriately sized volumetric pipet, the exact volume of the stock solution as indicated in Table II below was transferred into a 100 ml flask for each dilute solution desired.

TABLE II

| Stock Solution (ml) | Rosin in final dilute solution (ppm) |
|---|---|
| 1 | 1 |
| 2 | 2 |
| 5 | 5 |
| 10 | 10 |
| 20 | 20 |
| 50 | 50 |

To each flask was added HPLC isopropanol to within about 0.5 inches of the calibration mark on its neck. The stoppered flask was vigorously shaken and inverted to thoroughly mix the solution. As before, the stoppered flask was allowed to sit for about 30 minutes to allow the liquid to drain from the neck. Then additional isopropanol was added dropwise to bring the volume just to the 100 ml mark and the stoppered flask was again vigorously shaken and inverted to thoroughly mix the contents.

Absorbance Measurement of Standard Solutions

A Perkin-Elmer Model 552 Ultraviolet-visible Spectrophotometer was used to measure the absorbance of the diluted solutions at about 242 nanometers (nm). The wavelength of the maximum absorbance for abietic acid, a major component and the primary absorbing species of gum rosin, has been published as 241.7 nm. The manufacturer's instructions for operating the spectrophotometer were followed, except that the clean empty quartz cells or cuvettes were placed in the instrument before the power was turned on so that the baseline calibration automatically carried out by the instrument when the power is turned on, would compensate and correct the baseline for any unequal or unmatched absorbance by the cells. The wavelength was set to 242 nanometers and the absorbance range to 3.0 absorbance units full scale. One curvette was filled with HPLC isopropanol from the reagent bottle to serve as the reference. It was placed in the reference compartment of the instrument. The second curvette was carefully rinsed three times with the solution to be measured, with complete removal by pipet of the rinse solution each time. The rinsed cell was filled with HPLC isopropanol from the reagent bottle and placed in the sample compartment of the instrument. The absorbance reading was taken from the digital display of the instrument. However readings may also be read from a strip chart recorder or may be obtained from a computer which is capable of receiving the analog output from the spectrophotometer. The absorbance measured for this "Blank" was used to correct for any contribution by the solvent to the absorbance measured for the extract solution containing the contaminant to be determined or "Sample". For purposes of constructing a calibration curve, a series of "Samples" was measured, where "Sample" was one of the standard solutions. The absorbance of the contaminant was equal to the measured absorbance of the "Sample" less that of the "Blank".

Construction of Calibration Curve

The absorbances of the contaminant, which is in this example gum rosin, obtained by taking the difference between absorbances measured for the "Sample" and "Blank" for each standard solution, were plotted versus the actual contaminant concentration in each standard solution. The points should fall on a straight line which passes essentially through zero. At higher concentrations the curve may be non-linear, but such high concentrations are unlikely to be encountered in actual measurement of contamination on "cleaned" ECAs.

Preparatlon of Specimen ECAs

The following defluxing solutions were used in the examples:

(A) a blend prepared of 5.7 wt % methanol, 0.25 wt % nitromethane, and 94 wt % Freon 113 similar to commercially available Freon TMS* manufactured by DuPont de Nemours, E. I. Co., and (B) a stabilized 1,1,1-trichloroethane and alcohol blend sold under the tradename Prelete* and manufactured by The Dow Chemical Company.

A series of 1 inch by 2 inches by 1/16 inch ECA's with three dual in-line packages were fluxed with one of the commercial flux solutions containing abietic acid as described in Table III below. The so fluxed board was heated to 240° C. for 15 seconds to flash off the flux solvent and reflow the organic solids, simulating the soldering step. The so fluxed board was then defluxed in one of the above defluxer solvents by immersing each board into the vapor over a boiling sump for 30 or 120 seconds then immersing the ECA into the boiling sump liquid for 30 or 120 seconds, withdrawing the board from the vapor zone and cooling to about ambient temperature then immersing the ECA into the vapor for 30 or 120 seconds. The board was removed from the vapor, cooled for 1 minute and then immersed into the extracting solutions of the present invention as set forth in Table III below of the representative results. At all times, the specimen ECAs were handled by tweezers or other like implements rather than by hands or fingers.

Preparation of the Extract Solutions

The volume of extracting solvent as indicated in Table III below was accurately measured by syringe and transferred into each of two clean plastic bags with zippered closures. In addition to the syringe any other method to deliver a precisely measured volume, such as pipet, buret, re-pipet and the like, could be used to measure and transfer the solvent. Likewise, any suitable container, preferably anti-static to prevent damage to the ECA from static discharge, could be used in place of the plastic bags. The volumes of extract solvent (in milliliters) were chosen to be integral multiples of the surface area for both sides (in square inches) of the specimen ECA to facilitate later computations. Also for convenience, the volumes were chosen such that the resulting concentration of the contaminant, in this case rosin flux residues, would fall within the linear portion of the calibration curve. The specimen ECA was placed into one of the bags containing the measured extracting solvent. The bag was then closed and folded to maximize contact between the solvent and the surface of the specimen. The bag containing only the solvent was closed and folded essentially identically to the one containing the specimen. Both bags were shaken for 10 minutes by a mechanical shaker, but they could also be shaken by hand. Experiments showed that 10 minutes was sufficient to extract 95% or more of the rosin flux contaminant. The ECA was removed from its bag of extract solution. The contents of each bag were poured into separately labelled clean glass sample bottles, with tightly screwed caps, for storage until the absorbance measurements were made, usually within a few hours.

Absorbance Measurement of Extract Solutions

The procedure was as described before for the standard solutions, except that the solution which had contacted the specimen ECA was called the "Sample" and the other one the "Blank". If the absorbance for the Sample was the same as that of the Blank, the entire procedure was repeated, except that another ECA and less volume of extracting solvent was used. Alternatively, if the absorbance for the contaminant (Sample absorbance less Blank absorbance) was found to lay on the non-linear portion of the calibration curves, the procedure was repeated, except that another ECA and a greater volume of the extracting solvent were used.

Calculation of Residual Rosin (μq/in)

Using the calibration curve in FIG. 4, the concentration of residual rosin was found which correlated to the absorbance difference of the Sample and Blank, called absorbance of the contaminant. The appropriate numerical values were then substituted in the following equation:

$$\text{Residual rosin}\left(\frac{\text{micrograms}}{\text{inch}^2}\right) = \frac{\left[\text{rosin concentration}\left(\frac{\text{micrograms}}{\text{gm solvent}}\right)\right] \times \left[\text{solvent sp. gr. or density (gm/ml)}\right] \times \left[\text{volume solvent (ml)}\right]}{\text{total surface area of board (inch}^2\text{)}}$$

scale, which corresponds to 10 inches on a chart recorder.

After 6 to 8 minutes, the recorder trace was stable. The Blank absorbance was measured on the chart in inches from zero. After recording the measurement, the pumps were turned off in the reverse order from which they were turned on.

Calibration Curve Construction with Rosin Flux Solids Standard Solution

The chamber was opened and 20 ml of a 100 ppm

TABLE III

| Test Assembly | Initial Flux (mg) Wt. after Reflow | Defluxer Designation | Vol. Extract[3] | Abs. (242 nm[4]) | ppm Rosin | μg/in² | % of Initial Flux |
|---|---|---|---|---|---|---|---|
| | | Alpha 711-35[1] Flux (30 second defluxing cycles) | | | | | |
| 1 | 21.0 | (A) Fluorocarbon | 40 cc 75% | 0.390 | 15.5 | 132 | 2.51 |
| 2 | 18.3 | 113, Methanol, | IPA/H₂O | 0.374 | 14.5 | 123 | 2.69 |
| 3 | 21.7 | Nitromethane | | 0.408 | 16.0 | 136 | 2.51 |
| 4 | 17.1 | Blend | | 0.380 | 15.0 | 128 | 2.99 |
| 5 | 18.6 | (B) Chlorinated | 40 cc 75% | 0.215 | 8.5 | 72 | 1.50 |
| 6 | 19.8 | Solvent Blend | IPA/H₂O | 0.263 | 10.5 | 89 | 1.80 |
| 7 | 30.4 | | | 0.282 | 11.0 | 94 | 1.20 |
| 8 | 17.2 | | | 0.247 | 10.0 | 85 | 2.00 |
| | | Kenco 465[2] Flux (120 second defluxing cycle) | | | | | |
| 9 | 16.0 | (A) Fluorocarbon | 12 cc IPA | 0.208 | 8.0 | 19 | 0.48 |
| 10 | 18.7 | 113, Methanol, | | 0.410 | 16.0 | 38 | 0.81 |
| 11 | 20.0 | Nitromethane | | 0.226 | 9.0 | 21 | 0.42 |
| 12 | 23.4 | Blend | | 0.456 | 18.0 | 42 | 0.72 |
| 13 | 26.0 | (B) Chlorinated | 8 cc IPA | 0.206 | 8.0 | 13 | 0.20 |
| 14 | 16.0 | Solvent Blend | | 0.137 | 5.0 | 8 | 0.20 |
| 15 | 21.4 | | | 0.219 | 8.5 | 13 | 0.24 |
| 16 | 17.1 | | | 0.146 | 5.5 | 9 | 0.21 |

Notes for Table III
[1] Manufactured by Alpha Metals, Inc.
[2] Manufactured by Kenco Industries, Inc.
[3] High Performance Liquid Chromatograph or Spectral grade isopropanol (IPA)
[4] Absorbance values have been corrected for solvent blank.

EXAMPLES 17–21

General Procedure

A commercially available ultraviolet spectrophotometer manufactured by Laboratory Data Control, a subsidiary of the Milton Roy Company, and sold under the tradename Spectromonitor III was used in the instant examples. The spectrometer was turned on and allowed to warm up or stabilize for about 15 minutes before its use. A 100 ml sample of HPLC grade isopropanol (Blank) sold by the J. T. Baker Chemical Company labeled "Baker Analyzed" was introduced to a sample chamber by means of a buret. The chamber lid was securely fastened and a circulation pump connected to the chamber was started to circulate the isopropanol through the chamber. An air pressure of 17–20 psi was used for the circulation pump. A high pressure pump (Waters Model 45 HPLC pump) was used to circulate a sidestream from the chamber circulation loop to the flow-cell of the spectrometer. The high pressure pump was started and its flow rate set to 3.0 ml/minute about 10 to 20 seconds after the circulation pump was started to prevent entrained air from blocking the tubing leading to the flow-cell of the ultraviolet spectrometer. The spectrometer output was set to 2.0 absorbance units full standard solution was added with a buret. The 100 ppm standard solution was prepared from the non-volatile portion of a commercial solder flux designated as Alpha 611F (manufactured by Alpha Metals, Inc.) and isopropanol. After the chamber lid was securely closed the pumps were started as described in the general procedure above. After 6 to 8 minutes, the maximum absorbance was measured in inches from zero on the chart. The pumps were then turned off. It was found that by taking the absorbances after 6 to 8 minutes, the value obtained was within 5% of the equilibrium value.

The above general procedure was repeated with several 20 ml aliquots of the standard solution and the results are described in Table IV under the designation "First Series". The data points of this experiment are plotted in FIG. 5. After collecting the data for the First Series, the chamber was drained of solvent and then, refilled with 100 ml of fresh isopropanol. Then the solvent was circulated for 10 minutes through the apparatus to rinse the chamber and the lines. This rinsing process was repeated as necessary to achieve a baseline absorbance essentially the same as the initial Blank.

Several calibration measurements were made following the same procedure outlined above for the First Series except that 1 ml aliquots rather than 20 ml aliquots were used and the spectrometer was set to 0.5 absorbance units full scale. The datapoints obtained for these series are described as "Second Series" and "Third Series" in Table IV below. The calibration curve shown in FIG. 5 was obtained by plotting the datapoints obtained from the calibration experiments above.

The close agreement in Absorbance for replicate solutions confirms the reliability and reproducibility of the analyzer.

TABLE IV

| Sample Series | Cumulative Volume Std. Added (ml) | Cal'd ppm Rosin[1] | Absorbance |
|---|---|---|---|
| First Series | 0 | 0 | 0 |
| (x) | 20 | 16.6 | 0.28 |
| 100 ml HPLC- | 40 | 28.5 | 0.52 |
| IPA | 60 | 37.5 | 0.71 |
|  | 80 | 44.0 | 0.86 |
|  | 100 | 50.0 | 0.97 |
|  | 120 | 54.5 | 0.08 |
|  | 140 | 58.0 | 1.17 |
|  | 160 | 61.5 | 1.23 |
| Second Series | 0 |  | 0 |
| (o) | 1 | 0.9 | 0.036 |
| 100 ml HPLC- | 2 | 1.96 | 0.060 |
| IPA | 3 | 2.91 | 0.086 |
|  | 4 | 3.85 | 0.106 |
|  | 5 | 4.76 | 0.129 |
|  | 10 | 9.09 | 0.198 |
|  | 15 | 13.0 | 0.265 |
| Third Series | 0 | 0 | 0 |
| (.) | 1 | 0.9 | 0.035 |
| 100 ml HPLC- | 2 | 1.96 | 0.055 |
| IPA | 3 | 2.91 | 0.080 |
|  | 4 | 3.85 | 0.108 |
|  | 5 | 4.76 | 0.125 |
|  | 10 | 9.09 | 0.203 |
|  | 20 | 16.6 | 0.33 |

[1]ppm Cal'd = $\frac{ml\ added}{cum.\ total\ ml} \times 100$ ppm for example, 20 ml added to 100 ml IPA yields $\frac{20}{120} \times 100 = 16.6$ ppm final

Calibration Curve Construction with Gum Rosin Standard Solution

Figure 6:
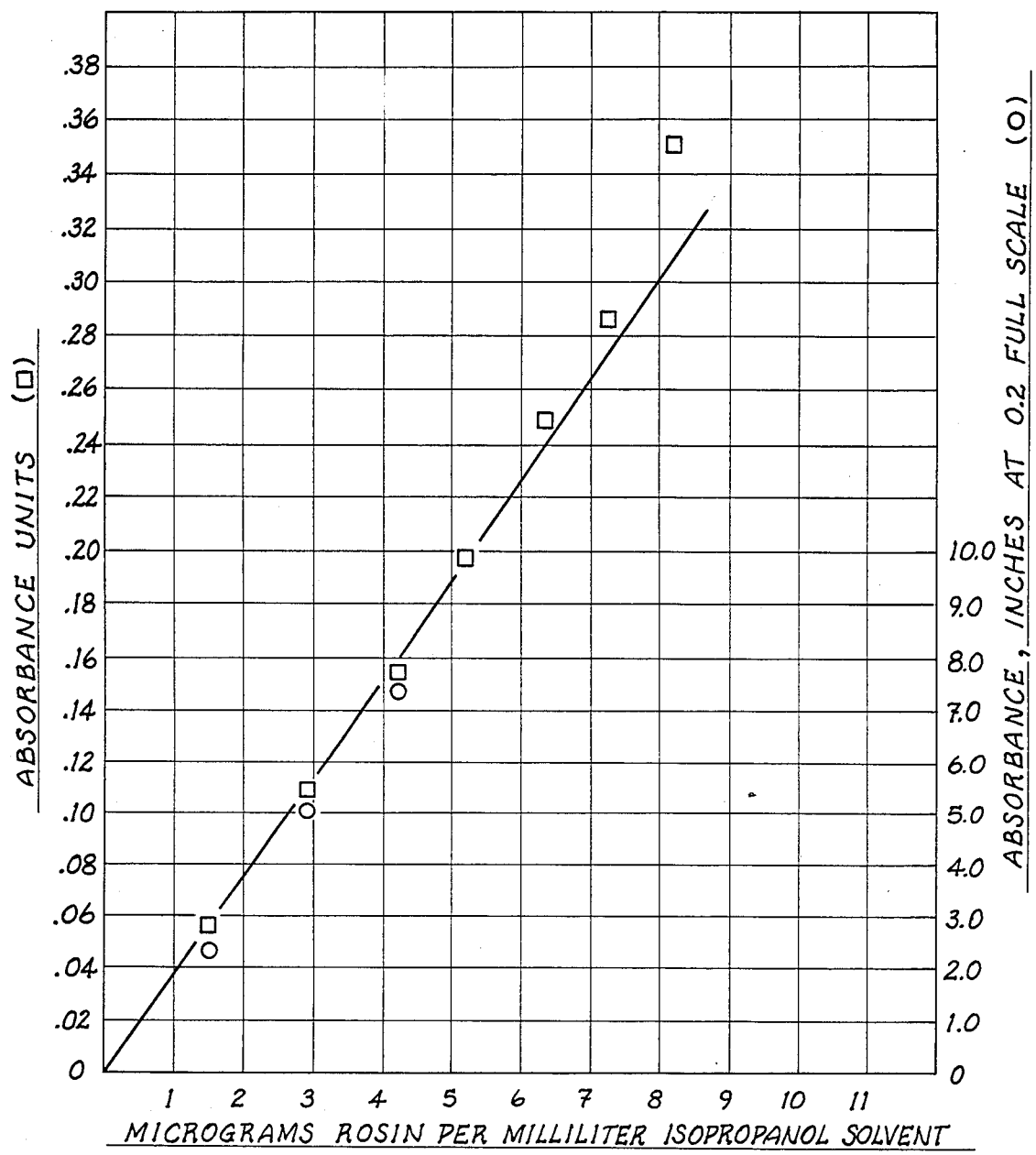
FIG. 6 represents a typical calibration curve showing micrograms of rosin per milliliter of solvent versus absorbance units.

The same procedure for obtaining the calibration curve using rosin flux standards described above was used except that 5 ml aliquots of a standard solution containing 31.7 μg gum rosin/ml isopropanol were used. The calibration curve for gum rosin is shown in FIG. 6.

Bare Circuit Boards

A number of circuit boards, 8 inches by 6 inches by 1/16 inch or 96 square inches, made from epoxy resin and fiberglass, commonly known in the electronics industry as FR 4, with no components and no circuitry, were sprayed lightly on one side, with one of two rosin solder fluxes as described in Table IV below. The boards were allowed to dry in air for 5 to 15 minutes. Thereafter the boards were heated in an oven for 15 seconds at 240° C., to simulate the effects of a soldering process. The boards were weighed and the dried solder found to range from 0.2 to 2.0 mg/in board. The boards were then defluxed or cleaned by exposure to vapors of the defluxing solvent described in Table IV in a custom-made portable stainless steel vapor defluxer. Four boards, at one time, were suspended in the vapor zone of the defluxer for the times indicated in Table III below. When the boards had cooled in air, but within 8 hours of the defluxing step, the residual rosin flux was measured separately for each individual board specimen.

The same procedures described above were used to measure the amount of residual rosin flux on the boards, except that in place of the addition of an aliquot of a standard solution, a board specimen was placed into the chamber where it was held in place by two vertical tracks. The results are described in Table V below.

TABLE V

| Flux | Defluxing Solvent | Deflux Time, min. | Number of Replicates | Absorbance, inches (Max-Blank) Mean | Std. Dev. | Residual[7] Rosin, μg/in² Mean | Std. Dev. |
|---|---|---|---|---|---|---|---|
| Alpha 611F[1] | Prelete ®[3] | 5 | 11 | 1.0 | ±0.3 | 1.6 | ±0.5 |
| Alpha 711-35[2] | Prelete | 5 | 5 | 1.3 | ±0.3 | 2.2 | ±0.4 |
| Alpha 711-35 | Freon TMS ®[4] | 5[5] | 3 | 2.1 | ±0.4 | 3.4 | ±0.7 |
| Alpha 711-35 | Freon TMS | 5.5[6] | 4 | 1.6 | ±0.3 | 2.7 | ±0.4 |
| Alpha 711-35 | Freon TMS | 5[6] | 5 | 1.0 | ±0.3 | 1.7 | ±0.5 |

Notes for Table V:
[1]Alpha 611F is a moderately activated rosin solder flux (RMA) manufactured by Alpha Metals, Inc.
[2]Alpha 711-35 is an activated rosin solder flux (RA) manufactured by Alpha Metals, Inc.
[3]Prelete ® is a blend of inhibited 1,1,1 trichloroethane and alcohols manufactured by The Dow Chemical Company.
[4]Freon TMS is a blend of trichlorotrifluoroethane, methanol and nitromethane manufactured by DuPont De Nemours, E.I., Co.
[5]See footnote 6.
[6]The relative energy into the heater was 30% greater than for (5).
[7]Calculated from calibration value (see FIG. 6) of 15.62 μg rosin in 100 ml. solvent per inches of chart:

$$\frac{Absorbance\ (inches) \times 15.62\ \mu g/inch = \mu g/inch^2}{surface\ area\ (in^2)}$$

EXAMPLES 22-25

Through-hole-type Assemblies

The same procedure of Examples 17-21 was followed, except that the specimen boards used in this series of examples were single-sided FR 4 boards of the through hole-type with six dual in-line packages. The size of the ECA was 5 inches by 2.5 inches by 1/16 inches or 25 sq. in. Only the side opposite the components was sprayed with the flux described in Table VI below. The defluxing solvent used in these examples was a stabilized 1,1,1-trichloroethane and alcohol blend sold under the tradename Prelete ®, manufactured by The Dow Chemical Company. A batch degreaser Model OP-5 manufactured by Branson Equipment Co., Clark, N.J., was used to contain the defluxing solvent, Prelete ®. The cleaning cycle consisted of exposing four boards at a time for 60 seconds in each of the following five stages in the defluxer: (1) immersion in the boiling solvent in the sump, (2) suspension in the vapor over the sump, (3) immersion in the warm solvent condensate (clean dip) compartment, (4) cooling in the air out of the defluxer, and (5) suspension in the vapor over the condensate compartment.

A special insert was used to suspend each specimen board in the test chamber of the instrument. After each measurement, the contaminated solvent was drained from the chamber and the valve left open for 3 minutes before reclosing the valve and adding the next 100 ml of isopropanol. The error in volume due to film remaining on the interior walls was determined to be less than 0.5 ml. Equilibrium values for the absorbance were routinely taken at 6 minutes when a flat horizontal maximum value was reached. Slight drifting in the recorder trace was corrected by cleaning the spray nozzles. The results are presented in Table VI below.

TABLE VI

| Flux | Number of Replicates | Absorbance, inches (Max-Blank) Mean | Std. Dev. | Residual Rosin, $\mu g/in^{2(4)}$ Mean | Std. Dev. |
|---|---|---|---|---|---|
| Alpha 611F[1] | 6 | 1.67 | ±0.33 | 3.5 | ±0.7 |
| Alpha 711-35[2] | 3 | 0.82 | ±0.16 | 1.7 | ±0.3 |
| Kenco 465[3] | 4 | 1.18 | ±0.14 | 2.5 | ±0.3 |
| None | 3 | 0.75 | ±0.09 | 1.6 | ±0.2 |

Notes for Table VI:
[1] Alpha 611F is a moderately activated rosin solder flux (RMA) manufactured by Alpha Metals, Inc.
[2] Alpha 711-35 is an activated rosin solder flux (RA) manufactured by Alpha Metals, Inc.
[3] Kenco 465 is an activated rosin solder flux (RA) manufactured by Kenco Industries, Inc.
[4] Calculated from calibration value (see FIG. 6) of 53 $\mu g$ rosin in 100 ml of solvent per inches of chart:

$$\frac{\text{Absorbance (inches)} \times 53\ \mu g/\text{inch}}{\text{surface area of sample (in}^2)} = \mu g/in^2.$$

EXAMPLES 26–29

Surface Mount Type Boards

The same procedure of Examples 17-21 was carried out, except that the specimen boards were single-sided FR 4 boards of the surface mounted-type with seven devices. The size of the boards was 3 inches by 2.5 inches by 1/16 inches or 14 square inches. The residual rosin was measured on two boards suspended at the same time in the analyzer chamber since the specimen boards were small. The total surface area per test sample was 28 square inches.

The cleaning cycle and residual rosin analysis used in these examples was the same as in Examples 22–25. The results are described in Table VII below.

TABLE VII

| Flux | Number of Replicates | Absorbance, inches (Max-Blank) Mean | Std. Dev. | Residual Rosin, $\mu g/in^{2(4)}$ Mean | Std. Dev. |
|---|---|---|---|---|---|
| Alpha 611F[1] | 4 | 1.33 | ±0.18 | 2.5 | ±0.4 |
| Alpha 611F | 3 | 1.88 | ±0.30 | 3.6 | ±0.6 |
| Alpha 711-35[2] | 4 | 0.79 | ±0.13 | 1.5 | ±0.3 |
| Kenco 465[3] | 3 | 1.88 | ±0.53 | 3.6 | ±0.8 |

Notes for Table VI:
[1] Alpha 611F is a moderately activated rosin solder flux (RMA) manufactured by Alpha Metals, Inc.
[2] Alpha 711-35 is an activated rosin solder flux (RA) manufactured by Alpha Metals, Inc.
[3] Kenco 465 is an activated rosin solder flux (RA) manufactured by Kenco Industries, Inc.
[4] Calculated from calibration curve value (see FIG. 6) of 53 $\mu g$ rosin in 100 ml of solvent per inches of chart:

$$\frac{\text{Absorbance (inches)} \times 53\ \mu g/\text{inch}}{\text{surface area of sample (in}^2)} = \mu g/in^2.$$

What is claimed is:

1. A method for determining organic contamination on an electronic circuit assembly (ECA) comprising:
   (a) contacting a previously defluxed ECA with a solvent adapted for removing organic contaminant species on the surface of the ECA,
   (b) measuring the spectral absorbance, in the ultraviolet or the visible region, of the organic contaminant species in the solvent contacted with the ECA, and
   (c) comparing the resultant absorbance units to a standard.

2. The method of claim 1 wherein step (b) is carried out with a spectrophotometer.

3. The method of claim 1 wherein step (b) is carried out with a spectrophotometer with a fiber optics probe.

4. The method of claim 1 including the step of cleaning the solvent by passing the solvent through an absorption column for removing organic contaminant species from the solvent.

5. A method for substantially automatically determining organic contamination on an electronic circuit assembly (ECA) comprising:
   (a) substantially continuously contacting a previously defluxed ECA with a solvent adapted for removing organic contaminant species on the surface of the ECA,
   (b) substantially continuously measuring the spectral absorbance, in the ultraviolet or visible region, of the organic contaminant species in a continuous stream of the solvent contacted with the ECA and,
   (c) comparing the resultant absorbance units to a standard.

6. The method of claim 5 wherein step (b) is carried out with a spectrophotometer.

7. The method of claim 5 wherein step (b) is carried out with a spectrophotomer with a fiber optics probe.

8. The method of claim 5 wherein the solvent is isopropanol.

9. The method of claim 5 wherein the organic contaminant species is rosin.

10. The method of claim 5 wherein the spectral absorbance of the organic contaminant species is within the range of about 190 nm to about 800 nm.

11. The method of claim 5 including the step of cleaning the solvent by passing the solvent through an absorption column for removing organic contaminant species from the solvent.

12. A method for determininq the cleanliness of an electronic circuit assembly (ECA) following defluxing to remove organic contamination on the ECA which comprises (a) washing the previously defluxed ECA by immersion and/or spraying with a measured quantity of a solvent, said solvent having a transparency for wave lengths in the UV or visible region, $$\text{Residual organic contaminant}\left(\frac{\text{micrograms}}{\text{inch}^2}\right) = \frac{\left[\text{organic contaminant concentration}\left(\frac{\text{micrograms}}{\text{gm solvent}}\right)\right] \times \left[\begin{array}{c}\text{solvent sp. gr. or}\\ \text{density (gm/ml)}\end{array}\right] \times \left[\begin{array}{c}\text{vol solvent}\\ \text{(ml)}\end{array}\right]}{\text{total surface area of board (inch}^2)}$$

Alternatively, $$\text{Residual organic contaminant}\left(\frac{\text{micrograms}}{\text{inch}^2}\right) = \frac{\left[\text{organic contaminant concentration}\left(\frac{\text{micrograms}}{\text{ml solvent}}\right)\right] \times \left[\begin{array}{c}\text{vol solvent}\\ \text{(ml)}\end{array}\right]}{\text{total surface area of board (inch}^2)}$$

(b) measuring the spectral absorbance of a stream of the wash solution by spectometry, and
(c) comparing the absorbance of said wash solution with a series of standard solutions containing known amounts of the contaminant thereby to provide a calibration curve conforming to Beer's Law, $A = abc$
   $A$ = absorbance
   $a$ = specific absorbance (molar absorptivity)
   $b$ = path length of light
   $c$ = concentration of absorbing species.

13. The method of claim 12 carried out substantially automatically and continuously.

14. The method of claim 12 including the step of cleaning the solvent by passing the solvent through an absorption column for removing organic contaminant species from the solvent.

15. A method for determining the cleanliness of a printed circuit electronic circuit assembly (ECA) board or printed wire assembly (board) (PCA, PCB) which consists of
   (a) immersing and/or spraying the ECA with a solvent solution;
   (b) agitating the solution,
   (c) measuring a stream of the solution in a calibrated spectrophotometer,
   (d) measuring a stream of an uncontaminated blank on the same calibrated spectrophotometer,
   (e) taking the difference between the later and the former, and
   (f) comparing the absorbance difference with that of a series of standard solutions containing known amounts of the contaminant thereby to provide a calibration curve conforming to Beer's Law, $A = abc$
   $A$ = absorbance
   $a$ = specific absorbance (molar absorptivity)
   $b$ = path length of light
   $c$ = concentration of absorbing species (g) calculating the micrograms of organic contaminant in the solution according to the following formula:

16. A method for determining the cleanliness of an electronic circuit assembly (ECA) following defluxing to remove organic contaminants on the ECA which comprises
   (a) washing a previously defluxed ECA by immersion and agitation in or by spray application of a measured quantity of a high purity polar organic solvent or aqueous, up to about 25 volume percent, deionized water solution of said solvent,
   (b) measuring by spectrophotometry the UV visible absorbance of a stream of said washing solution,
   (c) measuring a stream of uncontaminated blank of the solvent under like conditions,
   (d) taking the difference between the two measurements;
   (e) comparing this difference with a calibration curve developed under similar conditions by measuring known contaminant quantities in the solvent and plotting them on a graph, the abscissa of which is the concentration in milligrams of organic species per gram of solution or micrograms of organic species per milliliter of solution and the ordinate is the absorbance units; and
   (f) determining the micrograms of organic species per square inch total surface area of the ECA according to the following formula:

$$\text{Residual organic contaminant}\left(\frac{\text{micrograms}}{\text{inch}^2}\right) = \frac{\left[\text{organic contaminant concentration}\left(\frac{\text{micrograms}}{\text{gm solvent}}\right)\right] \times \left[\begin{array}{c}\text{solvent sp. gr. or}\\ \text{density (gm/ml)}\end{array}\right] \times \left[\begin{array}{c}\text{vol solvent}\\ \text{(ml)}\end{array}\right]}{\text{total surface area of board (inch}^2)}$$

Alternatively, $$\text{Residual organic contaminant}\left(\frac{\text{micrograms}}{\text{inch}^2}\right) = \frac{\left[\text{organic contaminant concentration}\left(\frac{\text{micrograms}}{\text{ml solvent}}\right)\right] \times \left[\begin{array}{c}\text{vol solvent}\\ \text{(ml)}\end{array}\right]}{\text{total surface area of board (inch}^2)}$$

17. An apparatus for determining the organic contamination of an electronic circuit assembly (ECA) comprising:
   (a) a means for contacting a previously defluxed ECA with a solvent adapted for removing organic contaminant species on the surface of the ECA,
   (b) a means for measuring the spectral absorbance, in the ultraviolet or the visible region, of the organic contaminant species in the solvent contacted with the ECA, and
   (c) a means for comparing the resultant absorbance units to a standard.

18. The apparatus of claim 17 wherein the means for measuring the spectral absorbance is a spectrophotometer.

19. The apparatus of claim 17 wherein the means for measuring the spectral absorbance is a spectrophotometer with a fiber optics probe.

20. The apparatus of claim 17 including a means for removing the organic contaminant species from the solvent for providing a reuseable solvent.

21. An apparatus for automatically determining the organic contamination of an electron circuit assembly (ECA) comprising:
   (a) a means for continuously contacting a previously defluxed ECA with a solvent adapted for removing organic contaminant species on the surface of the ECA,
   (b) a means for continuously measuring the spectral absorbance, in the ultraviolet or visible region, of the organic contaminant species in a continuous stream of the solvent contacted with the ECA,
   (c) a means for comparing the resultant absorbance units to a standard.

22. The apparatus of claim 21 wherein the means for measuring the spectral absorbance is a spectrophotometer.

23. The apparatus of claim 22 wherein the spectrophotometer contains a flow-through cell.

24. The apparatus of claim 21 wherein the means for measuring the spectral absorbance is a spectrophotometer with a fiber optics probe.

25. The apparatus of claim 21 wherein the solvent is isopropanol.

26. The apparatus of claim 21 wherein the organic contaminant species is rosin.

27. The apparatus of claim 21 wherein the spectral absorbance of the organic contaminant species is within the range of about 190 nm to about 800 nm.

28. The apparatus of claim 21 including a means for removing the organic contaminant species from the solvent for providing a reuseable solvent.

29. An apparatus for quantitatively measuring residual organic contaminant species on electric circuit assemblies (ECA) comprising:
   (a) a vessel having a chamber adapted for receiving an ECA and receiving a measured quantity of a washing solvent for washing the ECA;
   (b) a means for recirculating washing solvent through the vessel chamber;
   (c) a means for receiving a side stream of the recirculated washing solvent and measuring the spectral absorbance of the organic contaminant species in the side stream; and
   (d) a means for recording the absorbance units of the sidestream.

30. The apparatus of claim 29 including a reservoir means for holding makeup washing solvent.

31. The apparatus of claim 29 including a filter for filtering any solid materials in the washing solvent before recirculation of the solvent.

32. The apparatus of claim 29 wherein the means for recirculating the washing solvent is a pump.

33. The apparatus of claim 29 including a means for recirculating the side stream of washing solvent to the vessel after measuring the absorbance levels of the sidestream.

34. The apparatus of claim 29 including a means for removing the organic contaminant species from the solvent for providing a reuseable solvent.

35. The apparatus of claim 29 including means for spraying washing solvent onto the ECA in the chamber.

36. The apparatus of claim 29 including a housing for enclosing the elements (a)–(d) of claim 28.

37. The apparatus of claim 36 including a display means on the housing.

38. The apparatus of claim 29 wherein the solvent is isopropanol.

39. The apparatus of claim 29 wherein the spectral absorbance of the organic contaminant species lies in the range of about 190 nm to about 800 nm.

* * * * *